United States Patent [19]
Pon et al.

[11] Patent Number: 6,015,895
[45] Date of Patent: Jan. 18, 2000

[54] LINKER ARM FOR SOLID SUPPORT OLIGONUCLEOTIDE SYNTHESIS AND PROCESS FOR PRODUCTION THEREOF

[75] Inventors: Richard T. Pon; Shuyuan Yu, both of Calgary, Canada

[73] Assignee: University Technologies International Inc., Canada

[21] Appl. No.: 09/091,513

[22] PCT Filed: Dec. 13, 1996

[86] PCT No.: PCT/CA96/00837

§ 371 Date: Jun. 19, 1998

§ 102(e) Date: Jun. 19, 1998

[87] PCT Pub. No.: WO97/23497

PCT Pub. Date: Jul. 3, 1997

Related U.S. Application Data

[60] Provisional application No. 60/009,208, Dec. 22, 1995.

[51] Int. Cl.[7] .......................... C07H 21/00; C07H 21/02; C07H 21/04
[52] U.S. Cl. .................. 536/25.3; 536/25.33; 536/25.34
[58] Field of Search .............................. 536/25.3, 25.33, 536/25.34

[56] References Cited

U.S. PATENT DOCUMENTS

| | | | |
|---|---|---|---|
| 5,736,626 | 4/1998 | Mullah et al. | 536/25.3 |
| 5,770,687 | 6/1998 | Hornik et al. | 530/311 |
| 5,777,077 | 7/1998 | Albericio et al. | 530/335 |
| 5,798,276 | 8/1998 | Haugland et al. | 436/546 |
| 5,817,751 | 10/1998 | Szardenings et al. | 530/317 |
| 5,817,811 | 10/1998 | Breiphol et al. | 544/264 |

FOREIGN PATENT DOCUMENTS

| | | |
|---|---|---|
| 9206103 | 4/1992 | WIPO . |
| 9307883 | 4/1993 | WIPO . |
| 9623497 | 7/1997 | WIPO . |

OTHER PUBLICATIONS

Pon et al.(I), "Hydroquinon–O,O'–Diacetic Acid as a More Labile Replacement for Succinic Acid Linkers in Solid–Phase Oligonucleotide Synthesis," *Tetrahedron Letters*, 38(19), 3327–3330 (May 12, 1997).

Pon et al.(II), "Rapid Automated Derivatization of Solid–Phase Supports for Oligonucleotide Synthesis Using Uronium or Phosphonium Coupling Reagents," *Tetrahedron Letters*, 38(19), 3331–3334 (May 12, 1997).

Pon et al.(III), "Hydroquinone–O,O'–Diacetic Acid ('Q–Linker') as a Replacement for Succinyl and Oxalyl Linker Arms in Solid Phase Oligonucleotide Synthesis," *Nucleic Acids Research*, 25(18), 3629–3635 (1997).

Tetrahedron, (incl. Tetrahedron Reports), vol. 44, No. 14, Oxford GB, pp. 4331–4338 XP000673489 T. Tanaka et al.

Biotechniques, vol. 6, No. 8, Jan. 1, 1998, pp. 768–770, 773–775, XP000562920, Pon R.T et al.

Biophosphates and Their Analogues, Synthesis, Structure, Metabolism and Activity, vol. 3, 1987, pp. 3–21, XP000671967 M.H. Caruthers et al.

*Primary Examiner*—L. Eric Crane
*Attorney, Agent, or Firm*—Fitzpatrick, Cella, Harper & Scinto

[57] ABSTRACT

A linker arm for solid support oligonucleotide synthesis, the linker arm comprising formula (1), wherein: $X^1$ is selected from the group consisting of —O—, —S—, —S(O)$_2$—, —C(O)— and —N(R$^{12}$)—; $R^{12}$ is selected from the group comprising hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group, $X^3$ is —O— or —N(H)—; $R^1$, $R^2$, $R^3$, $R^4$ and $R^5$ are the same or different and are selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; n is 0, 1 or 2; and one of A' and B' is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, and the other of A' and B' has formula (2), wherein $X^2$ is selected from the group consisting of —O—, —S—, —S(O)$_2$— and —N(R$^{13}$)—; $R^{13}$ is selected from the group comprising hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group; $R^6$ and $R^7$ are the same or different and are selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; p is 0 or 1; and m is 0, 1 or 2. A process for producing the linker arm is also disclosed. The linker arm is useful in solid support oligonucleotide synthesis and is characterized by a desirable combination of stability against spontaneous hydrolysis and ease of intentional cleavage of the synthesized oligonucleotide from the linker arm.

40 Claims, 1 Drawing Sheet

LINKER ARM FOR SOLID SUPPORT OLIGONUCLEOTIDE SYNTHESIS AND PROCESS FOR PRODUCTION THEREOF

This application claims priority to the U.S. Provisional Application No. 60/009,208, filed Dec. 22, 1995.

TECHNICAL FIELD

The present invention relates to a linker arm for solid support oligonucleotide synthesis and to a process for production thereof.

BACKGROUND ART

The art of organic chemistry on solid supports is generally known. A useful review article on this topic may be found in "Organic Chemistry on Solid Supports"by Früchtel et al., *Angew. Chem. Int. Ed. Engl.*, 1996, 35, pgs. 17–42, the contents of which are hereby incorporated by reference.

As discussed in Früchtel et al., the art has developed automated solid-phase synthesis of polypeptides, oligonucleotides and oligosaccharides. Of particular interest here is solid-phase synthesis of oligonucleotides. The following are useful review articles/textbooks on this topic:

Beaucage et al., *Tetrahedron*, 1992, 48, pg. 2223;

Beaucage et al., *Tetrahedron*, 1993, 49, pgs. 6123–6194

Davis et al., *Innovation and Perspectives in Solid Phase Synthesis* (Ed.: R. Epton), Intercept, Andover, 1992, pg. 63; and Montserra et al., *Tetrahedron*, 1994, 50, pg. 2617; the contents of each of which are hereby incorporated by reference.

In the solid-phase synthesis of oligonucleotides, it is known to synthesize the oligonucleotide on an inorganic solid support bearing a succinyl linker arm—see, for example, any of the following references:

Caruthers et al., *Genetic Engineering*, Plenum Press, New York (1982), Vol. 4, pgs. 1–17;

Letsinger et al., *Genetic Engineering*, Plenum Press, New York (1985), Vol. 5, pg. 191;

Froehler et al., *Nucleic Acids Research*, 14:5399–5407 (1986); and

Matteucci et al., *Journal of American Chemical Society*, 103:3185–3186 (1981); the contents of each of which are hereby incorporated by reference.

Typically, the succinyl linker arm has the following general formula:

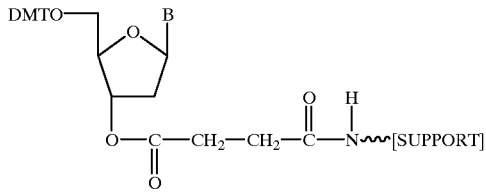

Thus, the succinyl group links the growing oligonucleotide from its terminal 3' hydroxyl group by an ester bond to a primary amine on the support, which may be, for example, conventional controlled pore glass (CPG) or silica, by an amide bond. Once the desired oligonucleotide has been synthesized, it is freed or cleaved from the succinyl linker arm hydrolyzing the ester carbonyl group. The hydrolysis agent is usually concentrated ammonium hydroxide. Typically, this reaction can take from 1–4 hours to complete. With improvements to current solid-phase oligonucleotide synthesizers, this cleavage step can represent 50% or more of the total time require to synthesize the desired oligonucleotide.

Thus, there have been various recent attempts in the art to develop improved linker arms for use in solid-phase oligonucleotide synthesis.

Of particular note is U.S. Pat. No. 5,112,962 [Letsinger et al. (Letsinger)], the contents of which are hereby incorporated by reference. Letsinger teaches a linker arm for solid support synthesis of oligonucleotides and oligonucleotide derivatives have the following formula:

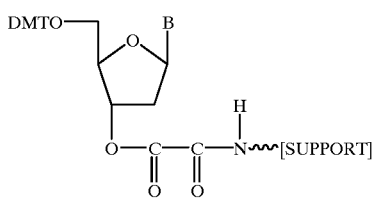

Thus, Letsinger teaches an oxalyl linker arm which purportedly release the synthesized oligonucleotide or oligonucleotide derivate in a period of 1–30 minutes in a manner that leaves the oligonucleotide fully protected. The oxalyl linker arm purportedly can be rapidly cleaved by 5% ammonium hydroxide in methanol, ammonium hydroxide, wet tertiary amine, triethylamine/alcohol, triethylamine/methanol, triethylamine/ethanol, aqueous trimethylamine and other bases. Unfortunately, the oxalyl linker arm of Letsinger suffers from its purported advantage. Specifically, the present inventors have discovered that the oxalyl linker arm of Letsinger is susceptible to significant spontaneous hydrolysis (e.g. spontaneous hydrolysis of approximately 10–40% per month) which renders it difficult it to use in commercial operations. This is illustrated in more detail hereinbelow. The oxalyl linker arm is also difficult to prepare because it requires using oxalyl chloride, which is highly reactive, toxic and dangerous.

Accordingly, the art is still in need of a linker arm capable of offering the advantages of the succinyl linker arm (ease of production/use) and the oxalyl linker arm (short cleavage time) while mitigating or obviating the advantages of both arms.

DISCLOSURE OF THE INVENTION

It is an object of the present invention to provide a novel linker arm for solid support oligonucleotide synthesis which obviates or mitigates at least one of the above-mentioned disadvantages of the prior art.

It is another object of the present invention to provide a novel process for producing a linker arm for solid support oligonucleotide synthesis.

Accordingly, in one of its aspects, the present invention provides a linker arm for solid support oligonucleotide synthesis, the linker arm comprising the following formula:

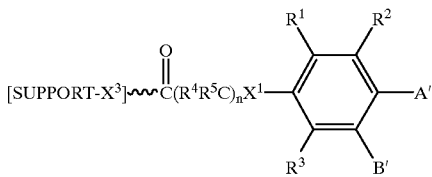

wherein: $X^1$ is selected from the group consisting of —O—, —S—, —S(O)$_2$—, —C(O)— and —N(R$^{12}$)—; $R^{12}$ is selected from the group comprising hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group; $X^3$ is —O— or —N(H)—; $R^1$, $R^2$, $R^3$, $R^4$ and $R^5$ are the same or different and are selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; n is 0, 1 or 2; and one of A' and B' is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, and the other of A' and B' has the formula:

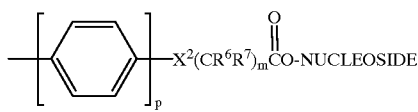

wherein $X^2$ is selected from the group consisting of —O—, —S—, —S(O)$_2$— and —N(R$^{13}$)—; $R^{13}$ is selected from the group comprising hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group; $R^6$ and $R^7$ are the same or different and are selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; p is 0 or 1; and m is 0, 1 or 2.

In another of its aspects, the present invention provides a process for producing a linker arm for solid support oligonucleotide synthesis, the process comprising the steps of:

reacting: (A) a linker compound of Formula (I):

(I)

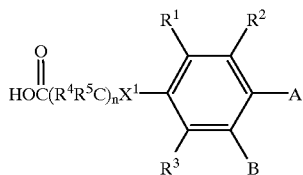

or derivate thereof, wherein: $R^1$, $R^2$ and $R^3$ are the same or different and are selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group; $R^4$ and $R^5$ are the same or different and are selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group; $X^1$ is selected from the group consisting of —O—, —S—, —S(O)$_2$— and —N(R$^{12}$)—; $R^{12}$ is selected from the group comprising hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group; n is 0, 1 or 2; and one or A and B is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group, and the other of A and B has the formula:

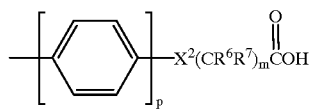

wherein p is 0 or 1, $X^2$ is selected from the group consisting of —O—, —S—, —S(O)$_2$— and —N(R$^{13}$)—, $R^{13}$ is selected from the group comprising hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group $R^6$ and $R^7$ are the same or different and are selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group, and m is 0, 1 or 2; or a compound of Formula II:

(II)

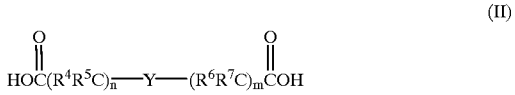

wherein Y is selected from the group consisting of —O—, —S—, —S(O)$_2$— and O—((CH$_2$)$_L$—O)$_q$, L is an integer less than or equal to 60, q is an integer in the range of 1–1000, and $R^4$, $R^5$, $R^6$, $R^7$, m and n have the same meaning as above, with the proviso that, when Y is O, at least one of n and m is 0 or 2; with (B) an OH of a desired nucleoside to produce a derivatized nucleoside having an ester linkage; and (C) a solid support, to produce the linker arm.

In another of its aspects, the present invention provides a process for producing a linker arm for solid support oligonucleotide synthesis, the linker arm comprising the following formula:

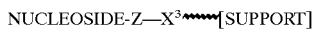

wherein $X^3$ is —O— or —N(H)—;

the process comprising the step of reacting together the compounds of Formulae III, IV and V:

wherein $X^3$ is as defined above, in the presence of an activating agent comprising at least one member selected from the group consisting of O-(7-azabenzotriazol-1-yl)-1,1,3,3-tetramethyluronium hexafluorophosphate (HATU), 2-(1H-benzotriazol-1-yl)-1,1,3,3-tetramethyluronium hexafluorophosphate, (HBTU), 1-hydroxybenzotriazole (HOBt) and mixtures thereof.

The present linker arm provides a desirable combination of: (i) ease of manufacture and use; (ii) negligible spontaneous hydrolysis (<5% per year); and (iii) fast (generally less than 5 minutes at room temperature) cleavage of the synthesized oligonucleotide.

As used throughout this specification, the term "oligonucleotide" is intended to have a broad meaning and encompasses conventional oligonucleotides, backbone- modified oligonucleotides (e.g. phosphorothioate, phosphorodithioate and methyl-phophonate analogs useful as oligotherapeutic agents) and oligonucleotide derivatives such as oligonucleotide-peptide conjugates.

BRIEF DESCRIPTION OF THE DRAWING

Embodiments of the present invention will be described with reference to the accompany drawing in which.

BEST MODE FOR CARRYING OUT THE INVENTION

Figure 1:
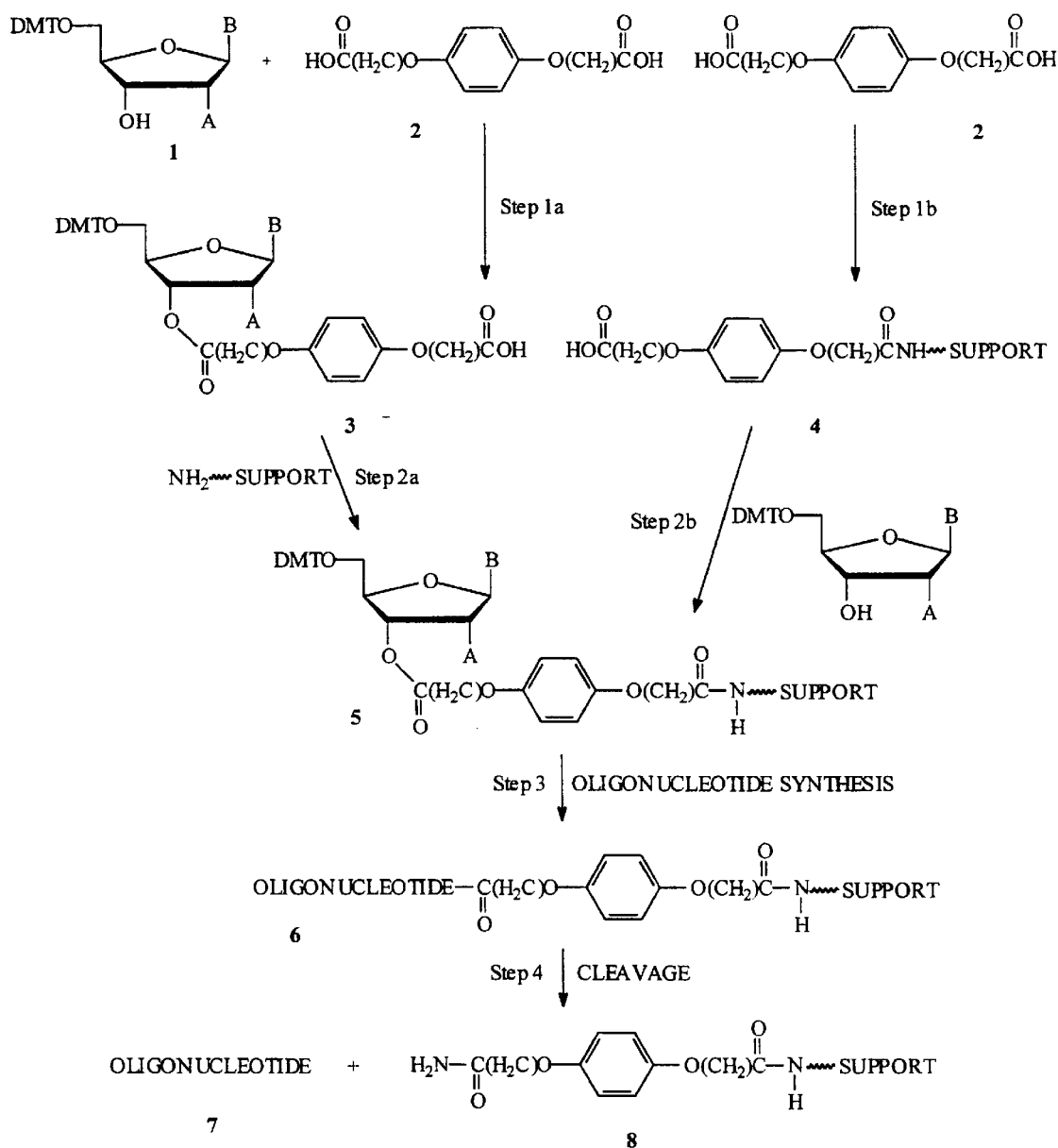
FIG. 1 illustrates a specific preferred embodiment of the process of the present invention.

Thus, the present inventors have discovered the use of a particular linking compound between the support and the starting nucleoside leads to an improved linker arm for solid support oligonucleotide synthesis.

In one embodiment, the linking compound is a compound of Formula I:

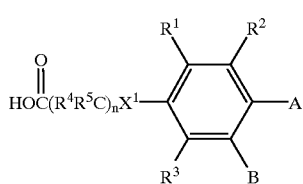

(I)

or derivate thereof, wherein: $X^1$ is selected from the group consisting of —O—, —S—, —S(O)$_2$—, —C(O)— and —N(R$^{12}$)—; R$^{12}$ is selected from the group comprising hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group; $R^1$, $R^2$, $R^3$, $R^4$ and $R^5$ are the same or different and are selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; n is 0, 1 or 2; and one of A and B is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, and the other of A and B has the formula:

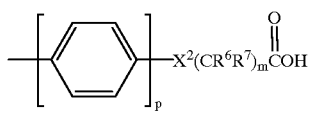

wherein p is 0 or 1, $X^2$ is selected from the group consisting of —O—, —S—, —S(O)$_2$—, —C(O)— and —N(R$^{13}$)—; R$^{13}$ is selected from the group comprising hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group, $R^6$ and $R^7$ are the same or different and are selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group, and m is 0, 1 or 2.

Throughout this specification, when reference is made to a substituted moiety, the nature of the substitution is not specification restricted and may be selected from the group consisting of a $C_1$–$C_{20}$ alkyl groups, a $C_5$–$C_{30}$ aryl group and a $C_5$–$C_{40}$ alkaryl group.

Preferably, B in Formula I is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, thereby rendering the acid-containing moieties in a "para" relationship.

Preferably, both $R^4$ and $R^5$ in Formula I are hydrogen, and both $R^6$ and $R^7$ in Formula I are hydrogen. More preferably, each of $R^4$, $R^5$, $R^6$, $R^7$, $R^{12}$ and $R^{13}$ in Formula I are hydrogen.

Preferably, at least one, more preferably both, m and n in Formula I are 1, and p in Formula I is 1.

Preferably, each of $R^1$, $R^2$ and $R^3$ in Formula I is hydrogen, and $X^1$ and $X^2$ in Formula I are both O.

The preferred linking compound of Formula I is hydroquinone-O,O'-diacetic acid. As is known in the art, the compound has the following structure:

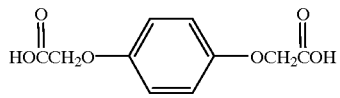

This is believed to be the first use of this acid to produce a linker arm for solid support oligonucleotide synthesis.

In another embodiment, the linking compound is a compound of Formula II:

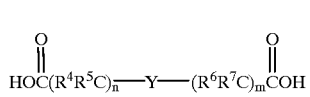

(II)

wherein Y is selected from the group consisting of —O—, —S—, —S(O)$_2$— and —O— ((CH$_2$)$_L$—O)—$_q$, L is an integer less than or equal to 60, q is an integer in the range of 1–1000, and $R^4$, $R^5$, $R^6$, $R^7$, m and n have the same meaning as above, with the proviso that, when Y is O, at least one of n and m is 0 or 2.

Preferably, L in Formula II is an integer in the range of 1–10, and q in Formula II is an integer in the range of 1–1000.

The most preferred compound of Formula II is thiodiglycolic acid (i.e. $R^4$=$R^5$=$R^6$=$R^7$=H, n=m=L and Y=S).

In the above formula defining the present linker arm, NUCLEOSIDE is a moiety selected from one of the following formulae:

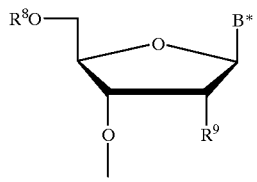

-continued

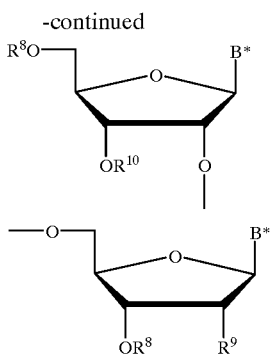

wherein $R^8$ and $R^{10}$ are the same or different and are hydrogen or a protecting group, $R^9$ is hydrogen (for deoxyribonucleosides or DNA) or —$OR^{11}$ (for ribonucleosides or RNA) wherein $R^{11}$ is hydrogen or a protecting group, and B* a nucleic acid base. Thus, in the case of RNA, there are two hydroxyl groups which may be protected. Also, the linker can be attached to either the 5'-, 3'- or (if ribose) 2'-hydroxyl positions. Indeed, for RNA sequences, it makes little difference whether the ester linker formed between the nucleoside and the linker compound is at the 2'- or 3'-hydroxyl position of the nucleoside. Thus, those of skill in the art will recognize that the nucleoside may be protected or blocked at the various of its hydroxyl moieties.

Non-limiting examples of useful protecting groups may be selected from the group consisting of trityl, methoxytrityl, dimethoxytrityl (DMT), dialkylphosphite, pivalyl-isobutyloxycarbonyl, t-butyldimethylsilyl, phenoxyacetal, 9-phenylxanthen-9-yl (pixyl), tetrahydropyranyl, methoxytetrahydropyranyl, methoxymethyl, benzyloxymethyl, methoxyethoxymethyl, methylthiomethyl, dialkylphosphate, levulinyl, dimethylphenylsilyl, trimethylsilyl, isopropyldimethylsilyl, diisopropylmethylsilyl, diethylisopropylsilyl, triisopropylsilyl, acetyl, benzoyl, pivaloyl, trifluoroacetyl, allyl, benzyl, o-nitrobenzyl, o-hydroxystyryldimethylsilyl, 2-oxo- 1,2-diphenylethyl, allyloxycarbonyl, monomethoxymethyl, nitroveratryloxycarbonyl, dimethoxybenzoin, dimethoxybenzoin carbonate, methylnitropiperonyl carbonate, fluorenylmethoxycarbonyl, 2-phenylsulfonylethoxycarbony, fluorophenylmethoxypiperidinyl and the like.

As is known in the art, the main prerequisite for the protecting group used on the 5'-hydroxyl position is the ability to be selectively removed without causing cleavage of the linker arm. Thus, the preferred protecting group for the 5'-hydroxyl position(s) is the acid labile dimethoxytrityl group. The main prerequisite for protecting groups on other hydroxyl positions, is stability to the conditions used for removal of the above protecting group. These latter protecting groups may be removed by the same conditions used to cleave the linker (discussed below) or separate conditions. The preferred protecting groups for these positions are trialkylsilyl (i.e. t-butyldimethylsilyl) or acetyl. Additional information may be obtained from the following references:

1. T. W. Greene and P. G. M. Nuts, "Protecting Groups in Organic Synthesis", Second Edition (1991), John Wiley and Sons, Inc., New York;
2. M. Schelhaas and H. Waldman, "Protecting Group Strategies in Organic Synthesis", Angew. Chemie Int. Ed. Engl. 35, 2056–2083 (1996);
3. M. J. Gait, ed., "Oligonucleotide Synthesis A Practical Approach", IRL Press, Oxford (1984);
4. S. A. Narang, ed., "Synthesis and Applications of DNA and RNA", Academic Press, Inc., Orlando (1987); and
5. S. Agrawal, ed., "Methods in Molecular Biology, Vol. 20: Protocols for Oligonucleotides and Analogs", Humana Press, Totowa, N.J. (1993);

the contents of each of which are hereby incorporated by reference, for a discussion of other possible hydroxyl protecting groups.

The manner by which the desired nucleoside may be protected is conventional and within the purview of a person skilled in the art. See, for example U.S. Pat. No. 3,400,190 (Melby), U.S. Pat. No. 4,458,066 (Caruthers et al.), the contents of each of which are hereby incorporated by reference.

A preferred method for production of deoxyribonucleosides in the context of the present invention is to use a nucleoside with a 5'-dimethoxytrityl protecting group and an appropriate exocyclic amino protecting group, e.g., $N^6$-benzoyl-5'-dimethoxytrityl-2'-deoxyadenosine, $N^4$-benzoyl-5'-dimethoxytrityl-2'-deoxycytidine, 5'-dimethoxytrityl-$N^2$-isobutyryl-2'-deoxyguanosine, or 5'-dimethoxytritylthymidine.

A preferred method for production of ribonucleosides in the context of the present invention is to use a 5'-dimethoxytrityl protected nucleoside, with appropriate exocyclic amino protection, and no protecting groups on either of the 2'- or 3'-hydroxyl positions. The linker can then react with either one of the two adjacent hydroxyl groups (it does not matter which) to give a mixture of 2'- and 3'-linkages. The unreacted hydroxyl groups may then be acetylated by treatment of the immobilized nucleoside with acetic anhydride. Alternatively, ribonucleosides which have a 5'-dimethoxytrityl group, appropriate exocyclic amino group protection, and either a 3'-hydroxyl protecting group or a mixture of 2'- and 3'-protecting groups can be used. The 3'-protected compounds are generally unwanted isomers which are simultaneously produced when the 2'-hydroxyl position is protected and have little other use.

In the above formula defining the present linker arm, the SUPPORT is a conventional solid support. The nature of the solid support is not particularly restricted and is within the purview of a person skilled in the art. Thus, the solid support may be an inorganic substance. Non-limiting examples of suitable inorganic substances may be selected from the group consisting of silica, porous glass, aluminosilicates, borosilicates, metal oxides (e.g. aluminum oxide, iron oxide, nickel oxide) and clay containing one or more of these. Alternatively, the solid support may be an organic substance such as a cross-linked polymer. Non-limiting examples of a suitable cross-linked polymer may be selected from the group consisting of polyamide, polyether, polystyrene and mixtures thereof. The preferred solid support for use herein is conventional and may be selected from controlled pore glass beads and polystyrene beads.

In the present process of producing the present linker arm, it is preferred to react the linker compound, the desired nucleoside and the solid support in the presence of an activating agent. As used throughout this specification, the term "activating group" is intended to have a broad meaning and is intended to encompass electrophilic reagents capable of activating a carboxyl moiety (e.g on the linking compound of Formula V) by attachment of a leaving group to the acyl carbon of the carboxyl moiety—see, for example, M. Bodanszky, "Principles of Peptide Synthesis", Second Edition, Springer-Verlag, Berlin (1993), the contents of which are hereby incorporated by reference. Thus, the activating agent should be capable of initiating at least one of the following: (a) formation of a reactive acylating agent (this is an example of a derivate) from the carboxyl moiety in a separate step or steps, followed by immediate treatment with the amino component (in this case, for example, an amino-terminated support) to form an amide linkage or a hydroxy component (in this case a hydroxy-terminated support or a hydroxyl group on the desired nucleoside) to form an ester linkage; (b) formation of an isolable acylating agent, separately, optionally with purification prior to treatment with the amino or hydroxy component as discussed in (a); and (c) formation of an acylating intermediate in the presence of the amino/hydroxy component, by the addition of an activating agent to a mixture of the two components. Thus, each of (a), (b) and (c) are applicable to the formation of both carboxylic esters and amides and all three routes can be used to attach nucleosides to supports.

For example, the Letsinger method, which first reacts oxalyl chloride with triazole, and then adds a nucleoside to the resulting oxalyl triazolide is an example of route (a). Conversion of the carboxylic acid group into an "active" ester using either p-nitrophenol, or di-, tri-, tetra-, or pentachlorinated or fluorinated phenols, or N-hydrosuccinimide are common examples of route (b). Route (c) has been the most commonly used method in recent years and both the carbodiimide reagents (dicyclohexylcarbodiimide, 1-(3-dimethylaminopropyl)-ethylcarbodiimide, and diisopropylaminocarbodiimide) and uronium reagents (O-(7-azabenzotriazol-1-yl)-1,1,3,3-tetramethyluronium hexafluorophosphate (HATU), 2-(1H-benzotriazol-1-yl)-1, 1,3,3-tetramethyluronium hexafluorophosphate, (HBTU)) may be used in this approach. Indeed, an aspect of the present invention relates to the discovery that the use of one or both of 1-hydroxybenzotriazole (HOBt), HATU or HBTU (preferably HBTU) in combination with 4-dimethylamino pyridine (DMAP) surprisingly and unexpectedly leads to relatively fast and high loading levels of the derivatized nucleoside on the solid support compared to the use of conventional activating agents (e.g. such as the combination of DMAP and 1-(3-dimethylaminopropyl)-ethylcarbodiimide (DEC)).

In a preferred embodiment, in addition to an activating reagent, the reaction of the linker compound, the desired nucleoside and the solid support is conducted in the presence of a nucleophilic catalyst or additive (typically 4-dimethylamino pyridine (DMAP), 1-hydroxybenzotriazole (HOBt), or 1-hydroxy-7-azabenzotriazole (HOAt)) to speed up the reaction and a tertiary amine base (typically triethylamine, pyridine, or diisopropylethylamine) to ionize the carboxylic acid group.

Thus, those of skill in the art will recognize that the precise nature of the activation agent is not particularly restricted provided, of course, that the activated carboxylic acid group is capable of initiating formation of the ester or amide linkage, as appropriate, and the activating reagent does not have any deleterious effect on the desired nucleoside.

Thus activation of the carboxylic acid by conversion into an acid chloride; an active ester (i.e. nitrophenyl, nitrophenylthio, trichlorophenyl, trifluorophenyl, pentachlorophenyl, pentafluorophenyl, or 3-hydroxy-2,3-dihydro4-oxo-benzotriazine esters); an active hydroxylamine ester (i.e. N-hydroxyphthalimide or N-hydroxysuccinimide); acid anhydride; or mixed anhydride will produce derivates which will form the desired linkage, and thus, these strategies are encompassed herein.

Non-limiting examples of activating agents may be selected from the group consisting of arylsulfonyl chlorides (e.g. benzenesulfonyl chloride (BS-Cl), mesitylenesulfonyl chloride (MS-Cl), triisopropylsulfonylchloride (TPS-Cl)); active arylsulfonyl esters (i.e. imidazole, triazole, nitrotriazole, or tetrazole esters of BS-Cl, MS-Cl or TPS-Cl); 2-ethoxy-1-(ethoxycarbonyl)-1,2-dihydroquinoline (EEDQ); acyl carbonates; 1,1'-(carbonyldioxy) dibenzotriazoles; chlorotrimethylsilane; carbodiimides (i.e. dicyclohexylcarbodiimide (DCC), 1-(3-dimethylaminopropyl)-ethylcarbodiimide (DEC), diisopropylcarbodiimide (DIC)) either alone or in combination with auxiliary nucleophiles (i.e. 1-hydroxybenzotriazole (HOBt), 1-hydroxy-7-azabenzotriazole (HOAt), N-hydroxysuccinimide (HOSu), or 3-hydroxy-3,4-dihydro-1,2,3-benzotriazin4-one (HOObt)) and/or catalysts (i.e. 4-dimethylaminopyridine (DMAP) or N-methylimidazole (NMI)); or uronium salts (i.e. tetramethyluronium chloride (TMU-Cl), 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-succinimido- 1,1,3,3-tetramethyluronium tetrafluoroborate (TSTU), 2-(3,4-dihydro-4-oxo-1,2,3-benzotriazin-3-yl)-1,1,3,3-tetramethyluronium tetrafluoroborate (TDBTU), 2-(2-oxo-1 (2H)-pyridyl-1,1,3,3-tetramethyluronium tetrafluoroborate (TPTU), 2-(5-norbornene-2,3-dicarboximido)-1,1,3,3 -tetramethyluronium tetrafluoroborate (TNTU), O-(7-azabenzotriazol-1-yl)-1,3-dimethyl-1,3-trimethyleneuronium hexafluorophosphate (HAMTU), O-(7-azabenzotriazol-1-yl)-1,1,3,3-bis(pentamethylene)uronium hexafluorophosphate (HAPipU), O-(7-azabenzotriazol-1-yl)-1,1,3,3-bis(tetramethylene)uronium hexafluorophosphate (HAPyU), O-(7-azabenzotriazol-1-yl)-1,1,3,3 -tetramethyluronium hexafluorophosphate (HATU)) either alone or in combination with auxillary nucleophiles (i.e. 1-hydroxybenzotriazole (HOBt), 1-hydroxy-7-azabenzotriazole (HOAt), N-hydroxysuccinimide (HOSu), or 3-hydroxy-3,4-dihydro- 1,2,3 -benzotriazin-4-one (HOObt)) and/or catalysts (i.e. 4-dimethylaminopyridine (DMAP) or N-methylimidazole (NMI)) will also produce the desired linkage.

Other examples of suitable activating reagents may be found in any of the following references:

M. Bodanszky, "Principles of Peptide Synthesis", Second Edition, Springer-Verlag, Berlin (1993);

J. Jones, "Amino Acid and Peptide Synthesis", Oxford University Press, Oxford (1992);

G. Grant, "Synthetic Peptides: A Users Guide", W. H. Freeman & Co., New York (1992);

E. Haslam, Tetrahedron, 36, pg. 2409, (1980); and

M. A. Ogliaruso and J. F. Wolfe, "Synthesis of Carboxylic Acids, Esters and Their Derivatives", John Wiley & Sons, Chicester (1991);

the contents of each of which are hereby incorporated by reference.

A preferred embodiment of the present process will now be discussed with reference to FIG. 1. In FIG. 1, DMT refers to dimethoxytrityl; B refers to a nucleobase and A is H (for deoxyribonucleosides) or OR (for ribonucleosides) wherein R is H or a blocking/protecting group such as described in the preceding paragraph. It should be clear that FIG. 1 is only a preferred embodiment provided for illustrative purposes only. In the following discussion, the reference numerals in parentheses correspond to the reference numerals in FIG. 1.

In one embodiment of the present process, the linker compound (2) is initially reacted with the desired nucleoside (1) to produce the derivatized nucleoside (3) and the derivatized nucleoside (3) is subsequently reacted with the solid support to produce the linker arm (5)—see Steps 1a and 2a in FIG. 1.

In another embodiment of the present process, the linker compound (2) is initially reacted with the solid support to produce a derivatized support (4) and the derivatized support (4) is subsequently reacted with the desired nucleoside (1) to produce the linker arm (5).

As shown in FIG. 1, in the linker arm (5), an ester linkage is formed between the nucleoside and the linker compound and an an amide linkage is formed between linker compound and the solid support. Of course, those of skill in the art will recognize that, if the support contained terminal hydroxyl groups, an ester linker would have been formed between the linker compound and the solid support.

As illustrated in Step 3 of FIG. 1, once the linker arm (5) has been produced, it may be used in the conventional manner to synthesize an oligonucleotide attached to the linker arm (6)—see, for example, U.S. Pat. No. 5,112,962 (Letsinger), incorporated by reference hereinabove.

At this point, the oligonucleotide may be cleaved from the solid support to yield the free oligonucleotide (7) and a used support (8)—see Step 6 in FIG. 1. The cleavage step usually comprises hydrolysis at the point of attachment of the initial nucleoside to the linking compound (i.e. the compound of Formulae I or II).

The reagent used to effect cleavage is not particularly restricted and is within the purview of a person skilled in the art. Preferably, the reagent is a weak base. Non-limiting examples of suitable reagents for this purpose may be selected from the group consisting of ammonium hydroxide, ammonium hydroxide/methanol, triethylamine/alcohol (e.g. ethanol, methanol, etc.), methylamine, dimethylamine, trimethylamine/water, methylamine/ammonium hydroxide, ammonia/methanol, potassium carbonate/methanol, t-butylamine, ethylenediamine and the like.

Cleavage can also be achieved using a solution of 20% piperidine in DMF at room temperature. Significantly, however, the rate of cleavage is slow ($t_{1/2}$~200 min) and so piperidine solutions can still be used to remove more sensitive protecting groups (such as the fluorenylmethoxycarbonyl (Fmoc) group) or to convert underivatized carboxylic acid groups into unreactive amides. The linker arm may also be cleaved under neutral conditions by treatment with room temperature fluoride ion (e.g. 1M tetrabutylammonium fluoride/THF or triethylamine trihydrofluoride).

The preferred cleavage method is treatment with concentrated aqueous ammonium hydroxide for 3 minutes at room temperature.

Embodiments of the invention will be illustrated in the following Examples which should not be construed as limiting the scope of the invention. In the Examples reference is made between various materials and FIG. 1. In the Examples, the following materials were used:

1. CPG, long chain alkylamine controlled pore glass, 120–200 mesh, 500 Å, 90–120 μmol/g of $NH_2$ groups), commercially available from CPG Inc. (Lincoln Park, N.J.);
2. HQPD, Hydroquinone-O,O'-diacetic acid, commercially available from Lancaster Synthesis Ltd. (Lancashire, England);
3. Ammonium hydroxide solutions (28–30%) and solvents were obtained from VWR Canlab (Edmonton, Alberta, Canada);
4. Cap A, a solution comprising acetic anhydride, 2,6-lutidine and tetrahydrofuran (THF) in a volume ratio of 1:1:8;
5. Cap B, a solution comprising N-methylimidazole and THF in a volume ratio of 16:84;
6. $I_2/H_2O$ oxidation, a solution comprising 0.05M $I_2$ in THF, $H_2O$ and pyridine in a volume ratio of 7:2:1;
7. Anhydrous pyridine and acetonitrile, distilled from $CaH_2$;
8. Anhydrous methanol, distilled from Mg turnings;
9. DMAP, 4-dimethylaminopyridine, reagent grade;
10. DIEA, anhydrous diisopropylethylamine distilled from $CaH_2$;
11. DEC, 1-(3-dimethylaminopropyl)-ethylcarbodiimide, reagent grade;
12. HBTU, 2-(1H-benzotriazol-1-yl)- 1,1,3,3-tetramethyluronium hexafluoro-phosphate, reagent grade;
13. HOBT, 1-hydroxybenzotrizole, reagent grade;
14. TEA, triethylamine, reagent grade;
15. $N^6$-benzoyl-5'-dimethoxytrityl-2'-deoxyadenosine-3'-O-hemisuccinate, $N^4$-benzoyl-5'-dimethoxytrityl-2'-deoxycytidine-3'-O-hemisuccinate, $N^2$-isobutyryl-5'-di-methoxytrityl-2'-deoxyguanosine-3'-O-hemisuccinate and 5'-dimethoxytritylthymidine-3'-O-hemisuccinate were obtained from the Sigma Chemical Co.;
16. Magnesium sulfate, reagent grade;
17. Oxalyl chloride; reagent grade;
18. Chloroform; reagent grade;
19. Dichloromethane, reagent grade; and
20. Succinyl-CPG, 89 μmol/g loading, was prepared from succinic anhydride and LCAA-CPG using the procedure of Damha et. al. (Nucl. Acids Res. 18, 3813, 1990).

In the following Examples the amount of nucleoside (loading) on the insoluble supports was determined by spectrophotometric trityl analysis. In this procedure, a sample of support (4–5 mg) was accurately weighed directly into a 10 mL volumetric flask. A solution of dichloroacetic acid in 1,2-dichloroethane in a volume ratio of 5:95 was then added to fill the flask. The contents were then thoroughly mixed and the absorbance of the orange coloured solution was measured at 503 nm using a Philips UV/V is spectrophotometer. The nucleoside loading (in μmol/g of CPG) was then calculated as:

$$Loading=(A_{503}\times Vol\times 1000)/(Wt\times 76)$$

wherein $A_{503}$=absorbance at 503 nm, Vol=solution volume in ml, and Wt=amount of CPG tested in mg. The accuracy of the trityl determination was approximately ±2–3%.

EXAMPLE 1

Synthesis of 5'-dimethoxytritylthymidine-3'-O-hemihydro-quinone-O,O'-diacetate (Step 1a in FIG. 1)

HQPA (10 mmol, 2.26 g), 5'-dimethoxytritylthymidine (10 mmol, 5.45 g), DMAP (1 mmol, 122 mg), DEC (10 mmol, 1.92 g), triethylamine (0.2 ml) and dichloromethane (50 ml) were combined in a 100 mL round bottomed flask and stirred at room temperature overnight. The solution was transferred to a separatory funnel, diluted with additional $CH_2Cl_2$ (50 ml), washed once with acidified $H_2O$ (150 ml $H_2O$ containing a few drops of 10% aqueous HCl), once with aqueous $NaHCO_3$ and twice with $H_2O$. The $CH_2Cl_2$ solution was dried over anhydrous MgSO$_4$, filtered, and then evaporated to give a light grey foam (95% yield). The crude material was checked by silica gel TLC (Rf=0.02, 5% methanol/CHCl$_3$; or Rf=0.08, 10% methanol/CHCl$_3$) and found to contain mostly desired product (compound 3 in FIG. 1). The remaining impurities contained unreacted nucleoside (Rf=0.39, 5% methanol/CHCl$_3$) and a faster moving impurity assumed to be the diester (Rf=0.54, 5% methanol/CHCl$_3$). The crude material was suitable for attachment to the support (Step 2a in FIG. 1) without further purification. However, purification by silica gel column chromatography using a 0–30% methanol/CHCl$_3$ gradient can be performed, if desired.

EXAMPLE 2

Synthesis of HOPA Derivatized CPG (Step 1b in FIG. 1)

CPG with 101 μmol/g amino loading (1 g), HQPA (1 mmol, 226 mg), DMAP (1 mmol, 122 mg), HBTU (1 mmol, 379 mg) and anhydrous pyridine (5 mL) were combined in a 20 ml screw-capped glass vial and shaken at room temperature (5 min). H$_2$O (1 mL) was added and shaking was continued (10 min). The CPG was filtered off, washed with methanol (~50 ml) and then CH$_2$Cl$_2$ (~50 ml), and then dried under vacuum. Heating (90° C., 5 min) a CPG sample (~1–2 mg) with 0.28 M ninhydrin/ethanol (100 μL) produced a negative result (colourless beads).

EXAMPLE 3

Attachment of 5'-dimethoxytritylthymidine-3'-O-hemihydro-quinone-O,O'-diacetate to CPG (Step 2a in FIG. 1) using DEC The unpurified nucleoside-3'-O-carboxylic acid product from Example 1 (2.0 mmol, 1.5 g), DMAP (0.5 mmol, 61 mg), DEC (5 mmol, 0.96 g), CPG (5 g), triethylamine (0.5 ml) and anhydrous pyridine (25 ml) were combined in a 100 mL round bottom flask and shaken at room temperature (4.5 hours). The CPG was filtered off, washed with methanol and then CH$_2$Cl$_2$. Unreacted amino groups were capped by treating the CPG with a 1:1 volume mixture of Cap A and Cap B solutions (2 hours) followed by washing with CH$_2$Cl$_2$ and drying. The nucleoside loading was determined by trityl analysis. Typical loadings were 30–40 μmol/g.

EXAMPLE 4

Attachment of 5'-dimethoxytritylthymidine-3'-O-hemihydro-quinone-O,O'-diacetate to CPG (Step 2a in FIG. 1) using HBTU/HOBT The unpurified nucleoside-3'-O-carboxylic acid product from Example 1 (0.05 mmol, 38 mg), HBTU (0.05 mmol, 19 mg), HOBT (0.05 mmol, 7 mg), CPG (500 mg), DIEA (0.1 mmol, 17 μl) and either anhydrous DMF, dichloromethane, acetonitrile, or pyridine (5 ml) were combined in a sealed flask and shaken at room temperature. CPG samples were removed at intervals for trityl analysis. After maximum loading was obtained (1 hour), the CPG was filtered off, washed with CH$_2$Cl$_2$, dried, and capped as described in Example 3. The nucleoside loading obtained at various intervals for each solvent is shown in Table 1.

EXAMPLE 5

Preparation of Highly Loaded 5'-dimethoxytritylthymidine CPG (Step 2a in FIG. 1)

The unpurified nucleoside-3'-O-carboxylic acid product from Example 1 (0.1 mmol, 76 mg), HBTU (0.1 mmol, 38 mg), HOBT (0.1 mmol, 14 mg), CPG (500 mg), DIEA (0.2 mmol, 34 μl) and anhydrous acetonitrile (3 ml) were combined in a sealed flask and shaken at room temperature. CPG samples were removed at intervals for trityl analysis. After maximum loading was obtained (1 hour), the CPG was filtered off, washed with CH$_2$Cl$_2$, and dried. The nucleoside loading obtained after 10, 20, 30 and 60 minutes coupling time was, respectively, 60.9, 64.8, 65.9, and 66.2 μmol/g.

TABLE 1

5'-Dimethoxytritylthymidine Loading Using HBTU/HOBT Coupling

| | Nucleoside Loading (μmol/g) | | | |
|---|---|---|---|---|
| Solvent | 10 min | 15 min | 30 min | 60 min |
| DMF | — | 31.4 | 32.6 | 32.7 |
| Dichloromethane | 36.7 | — | 41.2 | 41.4 |
| Acetonitrile | 39.7 | — | 41.2 | 41.4 |
| Pyridine | — | 40.1 | 41.3 | 42.6 |

EXAMPLE 6

Attachment of 5'-dimethoxytritylthymidine to HOPA Derivatized CPG (Step 2b in FIG. 1)

5'-Dimethoxytritylthymidine (0.1 mmol, 54 mg), HBTU (0.1 mmol, 38 mg), DMAP (0.1 mmol, 12 mg), the HQPA-CPG prepared in Example 2 (250 mg) and anhydrous acetonitrile (1 ml) were combined in a screw-capped glass vial and shaken at room temperature (2 h). The CPG was filtered off, washed with CH$_2$Cl$_2$ and dried. Trityl analysis showed a loading of 42.9 μmol/g.

EXAMPLE 7

Use of the Nucleoside-HOPA-CPG Support in Automated Oligonucleotide Synthesis

The nucleoside derivatized CPG (compound 4 in FIG. 1) was used in an identical fashion to conventionally derivatized CPG, i.e. the CPG was packed into plastic synthesis columns (~12 mg/column) and attached to a Perkin-Elmer Applied Biosystems 394 automated DNA synthesizer loaded with conventional synthesis reagents. Oligonucleotide synthesis was performed using an unmodified 0.2 μmol scale synthesis cycle. However, the wait steps in the conventional automated end procedure (Table 2) were modified to shorten the total cleavage time from 60 minutes to 3 minutes. The ammonium hydroxide solution containing the synthetic oligonucleotide was then heated (50° C., 16 hours) to finish deprotection of the oligonucleotide, in the conventional manner.

TABLE 2

Automated End Procedure Program For An PE/ABD 394 DNA Synthesizer

| Step # | Function Name | Function Number | Time (sec) |
|---|---|---|---|
| 1 | Begin | 106 | |
| 2 | 18 to column | 42 | 20.0 |
| 3 | Reverse Flush | 2 | 10.0 |
| 4 | Prep 10 | 115 | 5.0 |
| 5 | 10 to Collect | 36 | 10.0 |
| 6 | 15 to Waste | 64 | 5.0 |
| 7 | Block Flush | 1 | 5.0 |
| 8 | Wait | 103 | 25.0 |
| 9 | 10 to Collect | 36 | 7.0 |

TABLE 2-continued

Automated End Procedure Program For
An PE/ABD 394 DNA Synthesizer

| Step # | Function Name | Function Number | Time (sec) |
|---|---|---|---|
| 10 | 18 to Waste | 64 | 5.0 |
| 11 | Block Flush | 1 | 5.0 |
| 12 | Wait | 103 | 28.0 |
| 13 | 10 to Collect | 36 | 7.0 |
| 14 | 18 to Waste | 64 | 5.0 |
| 15 | Block Flush | 1 | 5.0 |
| 16 | Wait | 103 | 28.0 |
| 17 | 10 to Collect | 36 | 7.0 |
| 18 | 18 to Waste | 64 | 5.0 |
| 19 | Block Flush | 1 | 5.0 |
| 20 | Wait | 103 | 28.0 |
| 21 | Flush to Colect | 36 | 9.0 |
| 22 | 10 to Collect | 36 | 9.0 |
| 23 | Flush to Colect | 36 | 9.0 |
| 24 | Reverse Flush | 2 | 10.0 |
| 25 | Block Flush | 1 | 4.0 |
| 26 | 18 to Waste | 64 | 5.0 |
| 27 | 18 to Column | 42 | 20.0 |
| 28 | Reverse Flush | 2 | 10.0 |
| 29 | Block Flush | 1 | 5.0 |
| 30 | 10 Vent | 100 | 5.0 |
| 31 | End | | |

Note: Reagents 10 and 18 are ammonium hydroxide and acetonitrile, respectively.

EXAMPLE 8

Oxalyl Linker Arm

Oxalyl chloride (2.5 mmol, 218 μl) was added to a stirred, room temperature solution of triazole (12.5 mmol, 863 mg) in anhydrous pyridine (25 mmol, 2.0 ml) and anhydrous acetonitrile (17.5 ml) in a septum sealed 50 ml vial. A solution of 5'-dimethoxytritylthymidine (2.5 mmol, 1044 mg) in anhydrous pyridine (2.5 ml) and acetonitrile (17.5 ml) was prepared in a second septum sealed vial. The nucleoside solution was then added, via syringe, to the first solution with constant stirring. After stirring 30–45 minutes, the solution was added to CPG (10 g) in a 100 ml flask. The contents of the flask were agitated for 30 minutes and then anhydrous methanol (50 ml) was added. After 5 minutes, the CPG was filtered off, washed with chloroform and dried. Thereafter, the CPG was capped with a mixture of Cap A and Cap B solutions in a volume ratio of 1:1 for 30 minutes, washed and dried. Nucleoside loadings of between 30–40 μmol/g were determined by trityl analysis.

EXAMPLE 9

Succinyl Linker Arm

Method A (as per Pon et. al., 1988, Biotechniques 6, 768–775)

5'-Dimethoxytritylthymidine-3'-O-hemisuccinate (0.2 mmol, 123 mg), CPG (1 g), DEC (2 mmol, 382 mg), DMAP (0.1 mmol, 12 mg), triethylamine (80 μl) and anhydrous pyridine (10 ml) were combined in a 100 ml round bottom flask and shaken at room temperature (30–60 min). The CPG was filtered off, washed with pyridine and then $CH_2Cl_2$ and dried. Nucleoside loadings of between 30–40 μmol/g were determined by trityl analysis.

Method B (as per U.S. Pat. No. 5,554,744 (Bhongle et al.)

HOBT (0.015 mmol, 2 mg), CPG (0.5 g), anhydrous acetonitrile (2 ml), anhydrous pyridine (0.1 ml) and diisopropylcarbodiimide (0.15 mmol, 24 μl) were combined in a screw-capped glass vial and shaken at room temperature (20 min). 5'-Dimethoxytritylthymidine-3'-O-hemisuccinate (0.05 mmol, 32 mg) was added to the vial and shaking was continued at room temperature overnight. The CPG was filtered off, washed with $CH_2Cl_2$ and dried. A nucleoside loadings of 68.4 μmol/g was determined by trityl analysis, Method C (as per Damha et. al. 1990. Nucl. Acids Res. 18, 3813–3821)

CPG (25 g), succinic anhydride (50 mmol, 5 g), DMAP (5 mmol, 610 mg) and anhydrous pyridine (110 ml) were combined in a 250 ml round bottom flask and shaken at room temperature (24 hours). The CPG was then filtered off, washed with methanol and chloroform, and dried.

The succinylated CPG, prepared above, (1 g), 5'-dimethoxytritylthymidine (0.1 mmol, 54 mg), DEC (1 mmol, 192 mg), DMAP (0.1 mmol, 12 mg), triethylamine (80 μl) and anhydrous pyridine are combined in a 100 ml round bottom flask and shaken at room temperature overnight. Pentachlorophenol (0.5 mmol, 135 mg) was added to the flask and shaking was continued for another day. Finally, piperidine (5 ml) was added and after shaking five minutes, the CPG was filtered off, washed with $CH_2Cl_2$, dried, and capped as in Example 3. Nucleoside loadings of between 30–40 μmol/g were determined by trityl analysis.

EXAMPLE 10

Stability Evaluation of Linker Arm

After derivatization with 5'-dimethoxytritylated nucleosides, with either oxalyl (Example 8) or HQPA (Examples 3–6) linker arms, the long chain alkylamine controlled pore glass (LCAA-CPG) supports were washed extensively with chloroform or dichloromethane to remove residual reagents. The supports were left to dry and then the nucleoside loading was determined by trityl analysis. The CPG was stored in sealed glass vials at room temperature until required.

The nucleoside content of the CPG samples was retested by washing a CPG sample (~50 mg) extensively with dichloromethane on a Buchner funnel to remove any nucleoside not covalently bonded to the support. This wash step was important, otherwise the subsequent trityl analysis could not distinguish between covalently linked (i.e. intact linkers) and non-covalently linked (i.e. cleaved linkers) nucleosides on the surface of the support. After drying, trityl analysis was performed on the freshly washed CPG. The newly measured nucleoside loading was compared to the initial loading to determine the extent of cleavage.

In the case of the oxalyl linker, six lots with original nucleoside loadings of ~40 μmol/g were examined and the results are shown in Table 3. In Table 3, "Elapsed Time" is the period of time elapsed after synthesis of the linker arm.

TABLE 3

Stability of Oxalyl Linker Arm

| Nucleoside | Initial Loading (μmol/g) | Elapsed Time (months) | Final Loading (μmol/g) | Percent Change |
|---|---|---|---|---|
| dG | 38 | 2 | 8 | −79% |
| dA | 46 | 5 | 10.5 | −77% |
| dG | 35 | 3 | 18 | −49% |
| dC | 47 | 5 | 33 | −30% |
| dC | 40 | 2 | 32 | −20% |
| T | 39 | 2 | 33 | −15% |

These results showed a large variation in the amount of cleavage, with ~10–40% cleavage per month. This was sufficient to convince us that the oxalyl linker was not satisfactory and further evaluation of this linker chemistry was halted.

Similar stability checks were performed on supports containing the HQPD linker and the results are provided in Table 4.

TABLE 4

Stability of HQPD Linker Arm

| Nucleoside | Initial Loading ($\mu$mol/g) | Elapsed Time (months) | Final Loading ($\mu$mol/g) | Percent Change |
|---|---|---|---|---|
| dA | 41 | 21 | 40 | −2% |
| dC | 42 | 21 | 40 | −5% |
| dG | 26 | 21 | 22 | −15% |
| T | 27.5 | 22 | 26.7 | −3% |

These results show very good stability for dA, dC and T nucleosides and ~0.7% cleavage/month for dG which is far superior to the results obtained on the oxalyl linker arm.

EXAMPLE 11

Coupling of 5'-Dimethoxytritylthymidine-3'-O-hemisuccinate to LCAA-CPG Using HBTU/DMAP 5'-Dimethoxytritylthymidine-3'-O-hemisuccinate (0.05 mmol, 32 mg) HBTU (0.05 mmol, 19 mg), DMAP (0.05 mmol, 6 mg), CPG, 101 $\mu$mol/g, (0.5 g), anhydrous acetonitrile (2 mL), and anhydrous pyridine (0.1 mL) were combined in a septum sealed glass vial and shaken at room temperature for five minutes. The CPG was then filtered off, washed with chloroform and dried. Trityl analysis showed a loading of 65.3 $\mu$mol/g.

In contrast, this was 95% of the loading obtained from an overnight reaction using the DIC/HOBT method of Bhongle et al. above and identical CPG and nucleoside.

EXAMPLE 12

Coupling of 5'-Dimethoxytritylthymidine to Succinyl-CPG Using HBTU/DMAP

5'-Dimethoxytritylthymidine (0.1 mmol, 54 mg), HBTU (0.1 mmol, 38 mg), DMAP (0.1 mmol, 12 mg), succinyl-CPG (250 mg) and anhydrous acetonitrile (1 ml) were combined in one screw-capped glass vial. A second vial containing 5'-dimethoxytritylthymidine (0.05 mmol, 37 mg), HBTU (0.05 mmol, 19 mg), DMAP (0.05 mmol, 6 mg), succinylated CPG, 89 $\mu$mol/g (250 mg) and anhydrous acetonitrile (1 mL) was also prepared. Aliquots of CPG (~10 mg) from each vial were removed at intervals, washed with $CH_2Cl_2$ and the loading was determined by trityl analysis and the results are reported in Table 5. After the last sample analysis, the remaining CPG was filtered off, washed with $CH_2Cl_2$ and dried.

EXAMPLE 13

Automated Coupling of Nucleoside-3'-O-hemisuccinates to LCAA-CPG

Either $N^6$-benzoyl-5'-dimethoxytrityl-2'-deoxyadenosine-3'-O-hemisuccinate (0.05 mmol, 38 mg), $N^4$-benzoyl-5'-dimethoxytrityl-2'-deoxycytidine-3'-O-hemisuccinate (0.05 mmol, 37 mg), or N2-isobutyryl-5'-dimethoxytrityl-2'-deoxyguanosine-3'-O-hemi-succinate (0.05 mmol, 37 mg), and DIEA (0.05 mmol, 9 $\mu$L) in a septum sealed vial were dissolved in anhydrous acetonitrile (1 mL). 5'-Dimethoxytritylthymidine-3'-O-hemisuccinate (0.05 mmol, 32 mg) and DIEA (0.05 mmol, 9 $\mu$L) in a septum sealed vial were dissolved in anhydrous $CH_2Cl_2$/acetonitrile, 1:1 by volume (1 mL). Each solution was then filtered through a 0.45 $\mu$m syringe filter and installed on either bottle position #5, 6, or 7 of a PE/ABD 394 automated DNA synthesizer. A similarly prepared solution of HBTU (0.1 mmol, 38 mg) and DMAP (0.1 mmol, 12 mg) in anhydrous acetonitrile (2 mL) was installed on bottle position #8 of the DNA synthesizer. LCAA-CPG (12 mg) was accurately weighed into a plastic synthesis column and installed on column position #1 of the DNA synthesizer.

TABLE 5

HBTU/DMAP Coupling of 5'-Dimethoxytritylthymidine to Succinyl-CPG

| Amount DMT-T (mmol) per gram of succinyl CPG | Coupling Time (min) | Loading ($\mu$mol/g) |
|---|---|---|
| 0.4 | 5 | 44.7 |
| 0.4 | 15 | 50.9 |
| 0.4 | 30 | 60.8 |
| 0.4 | 60 | 58.8 |
| 0.4 | 120 | 67.2 |
| 0.2 | 5 | 15.2 |
| 0.2 | 15 | 17.1 |
| 0.2 | 30 | 18.3 |
| 0.2 | 60 | 19.0 |

1. Use of HATU/DMAP instead of HBTU/DMAP produced similar results. i.e. there was no advantage to using the more powerful HATU reagent.
2. The above coupling reaction was also performed using HBTU/HOBT and 0.2 mmol/g of DMT-T. However, the reaction was only half as fast and after 30, 60, and 120 min, the respective loadings were 6.5, 13.0, and 25.6 $\mu$mol/g.

A custom user procedure to simultaneously deliver the contents of one of either bottles # 5, 6, or 7, and the contents of bottle #8 to a synthesis column was defined, as per the PE/ABD 394 user manual. A custom begin procedure was defined to: 1, wash the synthesis column by filling with acetonitrile and flushing with argon (4×); 2, fill the column with nucleoside-3'-O-hemisuccinate and HBTU/DMAP solutions, using the above custom user procedures, for 4.0 seconds; and 3, wash the synthesis column by filling with acetonitrile and flushing with argon (4×). A sample listing for a begin procedure which contains user defined procedure #200 to deliver both bottles #7 and #8 simultaneously to synthesis column #1 is shown in Table 6. After completion of the begin procedure, an unmodified 0.2 $\mu$mole scale synthesis cycle was automatically initiated to perform oligonucleotide synthesis by the conventional method. The loading on the CPG was determined by: 1, collecting the first trityl colour, using an attached fraction collector; 2, diluting the colour to 25.0 ml with dichloroacetic acid in 1,2-dichloroethane (5:95, by volume); 3, measuring the absorbance (503 nm); and calculating the loading using the following equation:

Loading($\mu$mol/g)=($A_{503}$×vol×1000)/(76×Wt)

where vol=volume in mL and Wt=amount of CPG in mg.

Nucleoside loadings of 45–53 $\mu$mol/g were obtained within the brief time (4 sec) required to fill the synthesis column with reagents (i.e. Table 6, step #13) and no waiting interval (i.e. Table 6, step #14) was required.

EXAMPLE 14

Automated Coupling of 5'-dimethoxytritylthymidine-3'-O-hemihydroquinone-O,O'-diacetate To LCAA-CPG Solutions of 0.01, 0.025, and 0.05 M 5'-dimethoxytritylthymidine-3'-O-hemihydroquinone-O,O'- diacetate and DIEA in anhydrous acetonitrile were prepared, filtered through a 0.45 μm syringe filter, and installed as bottle #7 on a PE/ABD 394 DNA synthesizer. Automated derivatization was performed as described in Example 13, using 0.01 M, 0.025M and 0.05 M HBTU and DMAP solutions. The 5'-dimethoxytritylthymidine loadings obtained from the 4 second reaction using 0.01, 0.025 and 0.05 M reagents were 13.4, 28.8, and 46.0 μmol/g.

TABLE 3.1

Custom Begin Procedure For a PF/ABD 394 DNA Synthesizer To Automatically Derivatize LCAA-CPG

| Step Number | Function # | Function Name | Step Time |
|---|---|---|---|
| 1 | 106 | Begin | |
| 2 | 64 | 18 to Waste[1] | 5.0 |
| 3 | 42 | 18 to Column | 20.0 |
| 4 | 2 | Reverse Flush | 10.0 |
| 5 | 42 | 18 to Column | 20.0 |
| 6 | 2 | Reverse Flush | 10.0 |
| 7 | 42 | 18 to Column | 20.0 |
| 8 | 2 | Reverse Flush | 10.0 |
| 9 | 42 | 18 to Column | 20.0 |
| 10 | 2 | Reverse Flush | 10.0 |
| 11 | 1 | Block Flush | 5.0 |
| 12 | 101 | Phos Prep | 10.0 |
| 13 | 200[2] | 7 and 8 to C1 | 4.0 |
| 14 | 103 | Wait | 0.0[3] |
| 15 | 2 | Reverse Flush | 5.0 |
| 16 | 42 | 18 to Column | 20.0 |
| 17 | 2 | Reverse Flush | 10.0 |
| 18 | 42 | 18 to Column | 20.0 |
| 19 | 2 | Reverse Flush | 10.0 |
| 20 | 42 | 18 to Column | 20.0 |
| 21 | 2 | Reverse Flush | 10.0 |
| 22 | 42 | 18 to Column | 20.0 |
| 23 | 2 | Reverse Flush | 10.0 |
| 24 | 1 | Block Flush | 5.0 |
| 25 | End | | |

[1]Bottle #18 contains anhydrous acetonitrile.
[2]Custom user function
[3]This step can be increased for slower coupling reactions.

What is claimed is:

1. A process for producing a chemically modified solid support for oligonucleotide synthesis, the process comprising the steps of:

reacting: (A) a linker compound of Formula (I):

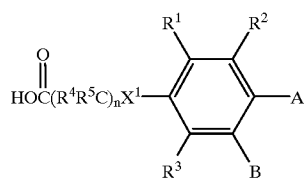

(I)

wherein: $R^1$, $R^2$ and $R^3$ are the same or different and are selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group; $R^4$ and $R^5$ are the same or different and are selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group; $X^1$ is selected from the group consisting of —O—, —S—, —S(O)$_2$— and —N($R^{12}$)—; $R^{12}$ is selected from the group consisting of hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group; n is 0, 1 or 2; and one of A and B is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group, and the other of A and B has the formula:

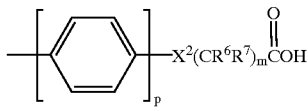

wherein p is 0 or 1, $X^2$ is selected from the group consisting of —O—, —S—, —S(O)$_2$—, —C(O)— and —N($R^{13}$)—, $R^{13}$ is selected from the group consisting of hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group, wherein $R^6$ and $R^7$ are the same or different and are selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group, and m is 0, 1 or 2; or a compound of Formula II:

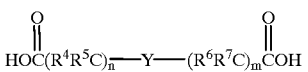

(II)

wherein Y is selected from the group consisting of —O—, —S—, —S(O)$_2$— and O—((CH$_2$)$_L$—O)$_q$, L is an integer less than or equal to 60, q is an integer in the range of 1–1000, and $R^4$, $R^5$, $R^6$, $R^7$, m and n have the same meaning as above, with the proviso that, when Y is O, at least one of n and m is 0 or 2; with (B) an OH of a desired nucleoside to produce a derivatized nucleoside having an ester linkage; and (C) a solid support capable of entering into an esterification reaction, to produce the linker arm.

2. The process defined in claim 1, wherein the linker compound is initially reacted with the desired nucleoside to produce the derivatized nucleoside and the derivatized nucleoside is subsequently reacted with the solid support to produce the linker arm.

3. The process defined in claim 1, wherein the linker compound is initially reacted with the solid support to produce a derivatized support and the derivatized support is subsequently reacted with the desired nucleoside to produce the linker arm.

4. The process defined in claim 1, wherein the linker compound is selected from Formula I.

5. The process defined in claim 4, wherein B is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group.

6. The process defined in claim 1, wherein the solid support is an organic substance.

7. The process defined in claim 1, wherein the desired nucleoside is reacted with a protecting group prior to reaction with the linker compound.

8. The process defined in claim 4, wherein each of $R^4$, $R^5$, $R^6$ and $R^7$ are hydrogen.

9. The process defined in claim 4, wherein m and n are both 1.

10. The process defined in claim 4, wherein p is 0.

11. The process defined in claim 1, wherein L is an integer in the range of 1–10.

12. The process defined in claim 1, wherein $R^{12}$ and $R^{13}$ are both hydrogen.

13. The process defined in claim 1, wherein each of $R^1$, $R^2$ and $R^3$ is hydrogen.

14. The process defined in claim 1, wherein $X^1$ and $X^2$ are both O.

15. The process defined in claim 1, wherein the solid support is an inorganic substance.

16. The process defined in claim 1, further comprising wherein the linker compound and the desired nucleoside are reacted in the presence of an activating agent which participates in the formation of the ester linkage.

17. The process defined in claim 16, wherein the activating agent is selected from the group consisting of arylsulfonyl chlorides, mesitylenesulfonyl chloride (MS-Cl), triisopropylsulfonylchloride (TPS-Cl)); active arylsulfonyl esters; 2-ethoxy-1-(ethoxycarbonyl)-1,2-dihydroquinoline (EEDQ); acyl carbonates; 1,1'-(carbonyldioxy) dibenzotriazoles; chlorotrimethylsilane; carbodiimides; and mixtures thereof.

18. The process defined in claim 16, wherein the activating agent is a uronium salt.

19. The process defined in claim 18, wherein the uronium salt is selected from the group consisting of tetramethyluronium chloride (TMU-Cl), 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-succinimido-1,1,3,3-tetramethyluronium tetrafluoroborate (TSTU), 2-(3,4-dihydro-4-oxo-1,2,3-benzotriazin-3-yl)-1,1,3,3-tetramethyluronium tetrafluoroborate (TDBTU), 2-(2-oxo-1 (2H)-pyridyl-1,1,3,3-tetramethyluronium tetrafluoroborate (TPTU), 2-(5-norbornene-2,3-dicarboximido)-1,1,3,3-tetramethyluronium tetrafluoroborate (TNTU), O-(7-azabenzotriazol-1-yl)-1,3-dimethyl-1,3-trimethyleneuronium hexafluorophosphate (HAMTU), O-(7-azabenzotriazol-1-yl)-1,1,3,3-bis(pentamethylene)uronium hexafluorophosphate (HAPipU), O-(7-azabenzotriazol-1-yl)-1,1,3,3-bis(tetramethylene)uronium hexafluorophosphate (HAPyU), and O-(7-azabenzotriazol-1-yl)-1,1,3,3-tetramethyluronium hexafluorophosphate (HATU)).

20. The process defined in claim 19, wherein the uronium salt is used in the presence of an auxiliary nucleophile.

21. The process defined in claim 20, wherein the auxiliary nucleophile is selected from the group consisting of 1-hydroxybenzotriazole (HOBt), 1-hydroxy-7-azabenzotriazole (HOAt), N-hydroxysuccinimide (HOSu), 3-hydroxy-3,4-dihydro-1,2,3-benzotriazin-4-one (HOObt), 4-dimethylaminopyridine (DMAP), N-methylimidazole (NMI) and mixtures thereof.

22. A linker arm for solid support oligonucleotide synthesis, the linker arm having the following formula:

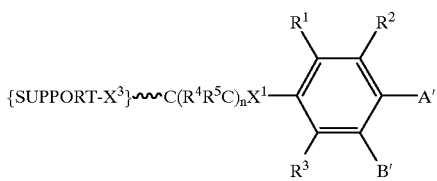

wherein:

$X^1$ is selected from the group consisting of —O—, —S—, —S(O)$_2$—, —C(O)— and —N(R$^{12}$)—; R$^{12}$ is selected from the group comprising hydrogen, a substituted or unsubstituted C$_1$–C$_{20}$ alkyl group, a substituted or unsubstituted C$_5$–C$_{30}$ aryl group and a substituted or unsubstituted C$_5$–C$_{40}$ alkaryl group; X$^3$ is —O— or —N(H)—; R$^1$, R$^2$, R$^3$, R$^4$ and R$^5$ are the same or different and are selected from the group consisting of hydrogen, halide, a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group; n is 0, 1 or 2; and one of A' and B' is selected from the group consisting of hydrogen, halide, a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group, and the other of A' and B' has the formula:

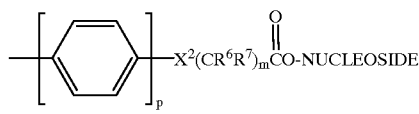

wherein X$^2$ is selected from the group consisting of —O—, —S—, —S(O)$_2$— and —N(R$^{13}$)—; R$^{13}$ is selected from the group comprising hydrogen, a substituted or unsubstituted C$_1$–C$_{20}$ alkyl group, a substituted or unsubstituted C$_5$–C$_{30}$ aryl group and a substituted or unsubstituted C$_5$–C$_{40}$ alkaryl group; R$^6$ and R$^7$ are the same or different and are selected from the group consisting of hydrogen, halide, a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group; p is 0 or 1; and m is 0, 1 or 2.

23. The linker arm defined in claim 22, wherein SUPPORT is an organic substance.

24. The linker arm defined in claim 22, wherein SUPPORT is an inorganic substance.

25. The linker arm defined in claim 22, wherein $X^1$ and $X^2$ are both O.

26. The linker arm defined in claim 22, wherein each of $R^1$, $R^2$, $R^3$, $R^{12}$ and $R^{13}$ is hydrogen.

27. The linker arm defined in claim 22, wherein both m and n are 1.

28. The linker arm defined in claim 22, wherein B' is selected from the group consisting of hydrogen, halide, a substituted or unsubstituted C$_1$–C$_{20}$ alkyl group, a substituted or unsubstituted C$_5$–C$_{30}$ aryl group and a substituted or unsubstituted C$_5$–C$_{40}$ alkylaryl group.

29. The linker arm defined in claim 22, wherein $R^4$ is hydrogen.

30. A process for producing a linker arm for solid support oligonucleotide synthesis, the linker arm having the following formula:

NUCLEOSIDE-Z—X$^3$-{SUPPORT} wherein X$^3$ is —O— or —N(H)—;

the process comprising the step of reacting together the compounds of Formulae III, IV and V:

wherein X$^3$ is as defined above and Z has the following formula:

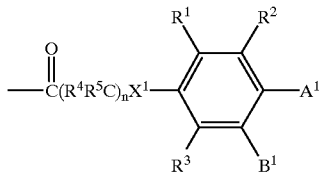

wherein: $X^1$ is selected from the group consisting of —O—, —S—, —S(O)$_2$—, —C(O)— and —N($R^{12}$)—; $R^{12}$ is selected from the group comprising hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group; $X^3$ is —O— or —N(H)—; $R^1$, $R^2$, $R^3$, $R^4$ and $R^5$ are the same or different and are selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; n is 0, 1 or 2; and one of $A^1$ and $B^1$ is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, and the other of $A^1$ and $B^1$ has the formula:

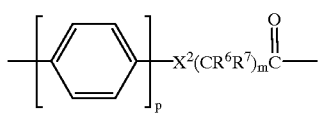

wherein $X^2$ is selected from the group consisting of —O—, —S—, —S(O)$_2$— and —N($R^{13}$)—; $R^{13}$ is selected from the group comprising hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group, $R^6$ and $R^7$ are the same or different and are selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; p is 0 or 1; and m is 0, 1 or 2, said step being conducted in the presence of an activating agent selected from the group consisting of O-(7-azabenzotriazol-1-yl)-1,3,3-tetramethyluronium hexafluorophosphate (HATU), 2-(1H-benzotriazol-1-yl)-1,1,3,3-tetramethyluronium hexafluorophosphate, (HBTU), 1-hydroxybenzotriazole (HOBt) and mixtures thereof.

31. The process defined in claim 30, wherein NUCLEOSIDE is a moiety selected from the group consisting of:

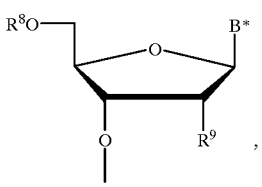

-continued

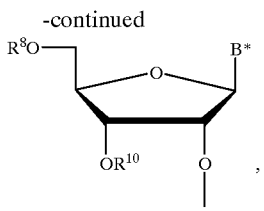

and

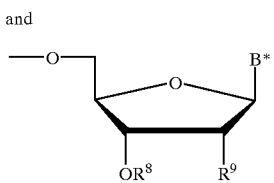

wherein $R^8$ and $R^{10}$ are the same or different and are hydrogen or a protecting group, $R^9$ is hydrogen or —O$R^{11}$ wherein $R^{11}$ is hydrogen or a protecting group, and B* is a nucleic acid base.

32. The process defined in claim 30, wherein SUPPORT is an organic substance.

33. The process defined in claim 30, wherein SUPPORT is an inorganic substance.

34. The process defined in claim 30, wherein $X^1$ and $X^2$ are both —O—.

35. The process defined in claim 30, wherein each of $R^1$, $R^2$, $R^3$, $R^{12}$ and $R^{13}$ is hydrogen.

36. The process defined in claim 30, wherein n and m are both 1.

37. The process defined in claim 30, wherein $R^4$ is hydrogen.

38. The process defined in claim 30, wherein the process is conducted in the presence of 4-dimethylamino pyridine (DMAP).

39. The process defined in claim 30, wherein the activating agent is 2-(1H-benzotriazol-1-yl)-1,1,3,3-tetramethyluronium hexafluorophosphate, (HBTU).

40. The process defined in claim 30, wherein $B^1$ is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkaryl group.

* * * * *